United States Patent [19]
Pader

[11] 4,100,269
[45] Jul. 11, 1978

[54] ANTICALCULUS DENTIFRICE

[75] Inventor: Morton Pader, Teaneck, N.J.

[73] Assignee: Lever Brothers Company, New York, N.Y.

[21] Appl. No.: 794,532

[22] Filed: May 6, 1977

Related U.S. Application Data

[63] Continuation of Ser. No. 374,351, Jun. 28, 1973, abandoned, which is a continuation of Ser. No. 125,389, Mar. 17, 1971, abandoned, which is a continuation-in-part of Ser. No. 800,008, Mar. 17, 1969, abandoned.

[51] Int. Cl.² .................. A61K 7/16; A61K 7/22; A61K 7/24; A61K 31/315
[52] U.S. Cl. .................. 424/49; 424/54; 424/55; 424/145; 424/289
[58] Field of Search .................. 424/49–58, 424/145, 289

[56] References Cited

U.S. PATENT DOCUMENTS

| 1,861,189 | 5/1932 | Pasternak | 424/49 |
|---|---|---|---|
| 1,943,467 | 1/1934 | Bley | 424/49 |
| 2,876,167 | 3/1959 | Manahan | 424/57 |
| 3,095,356 | 6/1963 | Moss | 424/49 |
| 3,175,951 | 3/1965 | Tucker et al. | 424/49 |
| 3,277,118 | 10/1966 | Schmid et al. | 260/347.7 |
| 3,622,662 | 11/1971 | Roberts et al. | 424/57 |
| 3,624,199 | 11/1971 | Norfleet et al. | 424/57 |

OTHER PUBLICATIONS

Khorosch, "Experience in the Use of Zinc for the Prophylaxis of Dental Caries", Stomatologia, V. 45, pp. 38–41, May–June, 1966.
Hanke, "Studies on the Local Factors in Dental Caries. I. Destruction of Plaques and Retardation of Bacterial Growth in the Oral Cavity", Journal of Am. Den. Assoc., pp. 1379 et seq., (Sep. 1940); (abstracted in Caries Research, pp. 333–334 (1950).
Steinberg, "Periodontal Disease–A Continued Report on Efficacy of a New Home Care Technique", J. Perio. V. 34, pp. 293–297 (May 1963); "Statistical and Clinical Evaluation", Dental Digest, V. 71, pp. 108 et seq. (May 1965).
Manley et al.; J. Dental Research V. 28, p. 169 (1949); Dental Abstracts, V. 7, pp. 527–528 (1962); Ludwick et al.; J. Amer. Dental Assoc. V. 43, pp. 285–289 (1951); Chem. Abstracts V. 58, entry 9364A (1963).

Primary Examiner—Shep K. Rose
Attorney, Agent, or Firm—Brumbaugh, Graves, Donohue & Raymond

[57] ABSTRACT

An improved method for the control of calculus is disclosed employing one or more insoluble zinc compounds as the active agent. Dentifrice formulations and mouthwash formulations for use in the novel method are also disclosed. The mouthwash compositions comprise from 1/10% to about 25% by weight of the zinc compound while the dentifrice compositions comprise 1/4% to about 25% by weight of said compound.

31 Claims, No Drawings

ANTICALCULUS DENTIFRICE

This application is a continuation of application Ser. No. 374,351 filed June 28, 1973 which, in turn, was a continuation of application Ser. No. 125,389 filed Mar. 17, 1971, which, in turn, is a continuation-in-part of application Ser. No. 800,008, filed Mar. 17, 1969, all now abandoned.

The present invention relates to a novel dentifrice formulation which is especially adapted to reduce calculus formation and to an improvement in the control of calculus.

Dental calculus is a hard, calcified formation which occurs on teeth. It is a function of the usual oral hygiene procedures such as regular tooth brushing to prevent the rapid buildup of calculus deposits. It is well known, however, that in the case of those prone to calculus formation even with the most regular and thorough brushing, calculus deposits will usually form in time and must be removed by a dentist.

It is generally believed that calculus originates with dental plaque. Plaque is the layer or deposit which forms on the surface of the teeth if one abstains from brushing for several days or brushes inadequately. Qualitatively speaking, it consists primarily of closely matted microorganisms embedded in a proteinaceous matrix of uncertain origin (but generally considered to be at least partially salivary) and containing epithelial cells and leucocytes. It is generally accepted by dental experts that clinical supragingival calculus (tartar) is a type of dental plaque which has crystallized with the formation of a hydroxyapatite crystalline structure. It will be apparent, therefore, that the incidence of calculus formation can be reduced by employing dental compositions which reduce or prevent the deposit of plaque or prevent the crystallization of dental plaque into the calculus stage.

A brief discussion of the pertinent prior art follows.

In U.S. Pat. No. 1,861,189, a tooth powder composition embodying patentee's invention is described as follows:

| | |
|---|---|
| Calcium gluconate | 100 parts |
| Zinc Citrate | 1 part |
| Flavoring | to suit |

The invention embodied in the above formulation concerned a dentifrice wherein the base used was improved so as not to irritate the gums and cause undesirable abrasion. This relatively non-abrasive dentifrice was obtained by using salts of gluconic acid and preferably calcium and magnesium gluconates as the base. However, it is worth noting that, despite great improvements in therapeutic and cosmetic attributes of dentifrices, virtually all dentifrices today still contain an abrasive to insure adequate cleansing of the teeth. Even those preparations reputed to be specially designed for sensitive teeth contain a minimum amount of abrasive. The calcium and magnesium gluconates of the Pasternack patent are relatively non-abrasive and consequently would be inoperable as substitutes for the abrasive material used in the present invention.

The Bley patent, U.S. Pat. No. 1,943,467 is directed to an improved antiseptic dentifrice composition wherein zinc carbonate, among others, is disclosed as a suitable base for the tooth powders or toothpastes, and wherein it is further disclosed that the amount of base ranges from about 60% to about 90% by weight. To utilize zinc carbonate or any of the zinc compounds disclosed herein, in the above amounts would produce an undesirable astringent effect.

In accordance with the present invention, a novel dental composition has been discovered which reduces the formation of dental calculus. The formulations of the present invention are characterized generally by the presence of certain physiologically acceptable zinc compounds in a concentration of between about 1/4% and 25% by weight of the formulation and a physiologically acceptable carrier medium therefor.

It is contemplated in the present invention that the carrier medium for the insoluble zinc compound may be either a mouthwash or a toothpaste or tooth powder formulation, such formulations being generally prepared in accordance with the art-recognized practice. In mouthwash formulations, for example, the carrier is typically an essentially aqueous solution of alcohol, glycerine or sorbitol. In some mouthwash formulations, it is not essential to use any of these materials although they do help to solubilize the flavor oils and can make the product smoother and impart body to it. They are also useful as an aid in sweetening the product. Surfactants or suspending agents are also present in mouthwash as solubilizers for essential flavor oils. The customary solubilizers for this purpose are the polyoxyethylene sorbitan fatty acid esters, sorbitan fatty acid esters and polyoxyethylene fatty acid esters. Thickening agents, such as cellulose ethers, may be incorporated to help maintain the zinc compound of this invention suspended.

In toothpaste and tooth powder formulations, the essential ingredient, other than the insoluble zinc compound, is a suitable dental abrasive. This abrasive must not interact with the zinc compound. Generally, therefore, the commonly used phosphate abrasives such as dicalcium phosphate dihydrate cannot be utilized in the present invention. Abrasives which contain calcium are also unsuitable in view of the fact that the presence of calcium contributes substantially to the formation of calculus; therefore, it would be inappropriate to utilize calcium abrasives in combination with the anti-calculus agents disclosed herein. It is further required that the abrasives used in the dentifrice formulation of the present invention provide a final composition which has a minimum dentin abrasion value of about 50. The Dentin Abrasion test is fully described in Example 7. In view of the foregoing, suitable dental abrasive substances include magnesium trisilicate, alumina and hydrates thereof, e.g., alpha alumina trihydrate, aluminum hydroxide, magnesium carbonate, calcined aluminum silicate, finely divided silicas, silica embedded in protective plastic particles, bentonite and plastic particles of appropriate size, hardness and composition for dentifrice abrasives. Such materials are preferred in the current invention. Toothpaste and tooth powder formulations also commonly contain a soap or synthetic surface active agent. It is essential in these formulations, as well as mouthwash formulations to provide sufficient foaming action to satisfy a marked consumer preference for this property. One preferred material for dentifrices is sodium lauryl sulfate. However, many other surface active agents can be used so long as they are compatible, i.e., do not interfere with the activity of the zinc compound.

In addition, the toothpaste formulation will contain humectants sufficient to provide smooth texture and flowability. Glycerine and sorbitol are preferred materials for this purpose together with suitable amounts of water, Ethyl alcohol, mineral oil, glucose, mannitol, propylene glycol, polyethylene glycols and other glycols can also be employed. Lastly, the toothpaste formulation will generally contain binding agents. These should be compatible with the zinc compound as well as with the other toothpaste components. Cellulose ethers are one type of preferred binder. Silica aerogels, precipitated silicas and pyrogenic or fumed silicas are another class of preferred binder.

Insoluble zinc compounds suitable for use in the present invention are those having a solubility of less than about one gm of zinc per 100 cc of water at 20° C. Preferably, the salt should have a solubility of not more than about 0.5 gm of zinc per 100 cc at 20° C. The zinc salt should, of course, be physiologically acceptable. Typical zinc compounds which may be used include the following materials:

Zinc tribromosalicylanilide
Zinc bacitracin
Zinc-2-hexyl-5-chlorosalicylanilide
Zinc soap of the $C_8$ to $C_{22}$ fatty acids
Zinc carbonate
Zinc benzoate
Zinc dl-lactate trihydrate
Zinc citrate
Zinc oxide
Zinc tetrafluoroborate
Zinc hexafluorosilicate
Zinc stannate
Zinc silicate It is believed that the important active constituent of the molecular structure in the foregoing compounds leading to anticalculus activity is the zinc ion. One theory which may explain the activity of zinc is the following:

Calculus formation may be described as occurring in several stages. In the first, saliva present in the mouth deposits a proteinaceous film on the tooth surfaces. Second, additional proteinaceous material deposits, accompanied by calcium and phosphate and various microbial populations, as well as mammalian cells derived from the oral tissues. The calcium and phosphate ions are present in the deposit substantially as amorphous calcium phosphate. This accumulation of microbial cells, mammalian cells, gelatinous proteinaceous matrix, calcium phosphate, and other elements is known as plaque. The last step to the development of calculus is the transformation of the calcium phosphate in the plaque from an amorphous form to a crystalline form. Calcification occurs in both the microbes themselves and in the interbacterial matrix. Crystalline development passes through a number of identifiable stages, the final stage being the formation of hydroxyapatite which may be easily characterized by X-ray diffraction analysis.

One should recognize that plaque is a complex system. Plaque in some people does not harden to form calculus. Why plaque is converted to calculus in one instance and not in another is a question only partially answered.

A possible theory explaining the action of zinc ion in the present invention is that zinc, if present before the final stage in which crystallinity of the calcium phosphate develops, interferes with the crystal development, and thereby prevents the formation of calculus. Partial evidence supporting this proposal is the fact that zinc interferes with the precipitation of calcium phosphate from a solution super-saturated with respect to calcium and phosphate ions.

It should be pointed out, however, that zinc may act by other mechanisms since the development of calculus can obviously be prevented by disruption of any one of the several steps outlined above. It is known particularly, for example, that zinc can have a significant influence on microbial systems; although there is at present no direct evidence that zinc will affect particular microorganisms which conceivably can contribute in a specific way to calculus formation, and calculus has been shown to occur in experimental animals in the absence of a microbial population.

While it is believed that the zinc ion generally possesses the property of reducing calculus formation, other considerations also affect the selection of suitable zinc compounds for use in the present invention. An important consideration in this respect is that the final product must not be so excessively astringent or irritating as to be unacceptable to the user. A number of soluble zinc compounds are known to be highly astringent, including zinc chloride, zinc acetate and zinc sulfate.

Another factor to be considered is the solubility of the zinc compound. Zinc compounds generally should have a solubility not exceeding about 0.5% to 1% by weight (based on the amount of dissolved zinc ion) at 20° C. An important reason for establishing an upper limit on the solubility of the preferred zinc compound is grounded in the fact that the more soluble zinc compounds tend to be astringent. Moreover, the concentration of the physiologically acceptable zinc compound used in the dentifrice formulation must be determined in light of the added requirement that the zinc compound provides no more than 5% insoluble zinc based on the total dentifrice formulation so that the final product is not excessively astringent or irritating to the user. Thus, if zinc carbonate were to be used, the concentration of said compound should be about 9% or less based on the total dentifrice formulation. While astringency is largely a subjective response, it is believed that the requirement that the zinc concentration not exceed about 5% by weight represents a reasonable upper limit.

Another advantage of using relatively insoluble zinc compounds is that through their use small quantities of these zinc compounds will become lodged in the cracks, crevices, and interstices between the teeth, as well as in dental plaque and other deposits, thereby promoting longevity of action. The insoluble zinc salts may provide a reservoir of this ion from which it is released over a prolonged period of time. Thus, activity can be maintained over the course of relatively long times and it is not necessary to resort to excessively frequent application. Such is extremely important when one considers consumer prophylaxis products. Manifestly, soluble zinc compounds will not be readily retained except to the extent that they are substantable to the enamel surfaces of the teeth and deposits thereon.

The concentration of zinc compound in the dental preparation used will be sufficient to realize the desired anticalculus effect. In general, a concentration of at least about 1/4% will be employed in dentifrices and 1/10% in mouthwashes. Concentrations of up to as much as 25% may be used depending on the formulation into which the zinc compound is incorporated, the nature of the zinc compound utilized, the physiological acceptability of the anion, etc. Typically, dentifrices and mouthwashes will have in the order of 0.1% to 10% by weight of the zinc compound.

The incidence of calculus may be reduced in accordance with the present invention through the regular use of the zinc salts had reduced the degree of formation of calculus. The results are set forth in Table 1. Data are given only for those subjects who finished all phases of the study.

TABLE I

| MEAN CALCULUS SCORES AND PERCENT REDUCTIONS | | | | | | |
|---|---|---|---|---|---|---|
| | | Phase I | Phase II | | Phase III | |
| | N | Baseline Score | Test Score | Percent Reduction | Test Score | Percent Reduction |
| Pepsodent T.P. + Placebo Rinse | 17 | 11.9 | 9.4 | 21.0 | 9.5 | 20.2* |
| Pepsodent T.P. + Zn Citrate, Zn TBS Rinse | 17 | 12.7 | 8.2 | 35.4 | 5.5 | 56.7** |

*Not significant
**Significant at $p. < 0.01$ use of a dentifrice or mouthwash of the foregoing description. Typically, application will be at least once daily through regular oral hygiene practices.

The present invention may be better understood by reference to the following examples:

EXAMPLE 1

A mouthwash formulation was prepared having the following composition:

| | |
|---|---|
| Zinc citrate | 5% |
| Zinc tribromosalicylanilide | 0.125% |
| Suspending agents | 1.00% |
| Flavor | 0.145% |
| Distilled water    q.s. | 100% |

The effectiveness of this mouthwash as an anti-calculus agent was evaluated in a group of fifty adult male subjects. Each member of the group was given an oral prophylaxis after having been chosen from a group of subjects previously selected on the basis of oral history, amount of calculus accumulations at the time of examination, general hygiene of the mouth, cleanliness of teeth, elapsed time since the last prophylaxis, brushing habits, etc. In order to insure proper participation by the subjects, they were instructed in proper procedures of oral care.

Phase I The subjects were then given a placebo oral rinse, a standard toothbrush and a standard commercial dentifrice (Pepsodent, a composition comprised of dicalcium phosphate dihydrate as an abrasive, humectant, and other common dentifrice ingredients). The subjects were requested to use the two products at least twice a day. At the end of a period of three months the calculus scores of the subjects were determined by the Volpe-Manhold method (*J. Periodontology*, Vol. 36, page 292 (1965).

Phase II The subjects were then divided into two comparable groups of 25 each, balanced with respect to calculus scores measured after three months' usage of the placebo products. The subjects were then given a second oral prophylaxis. One group was allowed to continue on their original oral hygiene routine, i.e., Pepsodent toothpaste plus a placebo mouthwash. The other group was instructed to continue the use of the nonactive dentifrice, but instead of a placebo oral rinse was supplied with an oral rinse in which was suspended a mixture of two insoluble zinc compounds, i.e., zinc tribromosalicylanilide (0.125%) and zinc citrate (5%). After three months on this regimen the subjects were scored for calculus formation.

Phase III The subjects were finally given another oral prophylaxis and the procedure repeated. The data were treated statistically to determine to what extent The effectiveness of further zinc compounds as anticalculus agents was assayed by means of several screening techniques. In general, it is believed that concurrent favorable results from several types of screening tests are desirable in order to indicate that a test compound possesses anticalculus activity.

The screening tests used for this purposes are the following:

(1) The *Leung Dipping Technique*. The Leung dipping technique is described in detail in the article by S. Wah Leung entitled, "A New Method for the In Vitro Production of Artifical Calculus", (*J. Periodontology*, Vol. 28, page 217 (1956)). The method was modified somewhat for improved quantitation of data, convenience, and correspondence of agent application with the oral use situation. The principle of the method is to dip glass plummets in and out of saliva (or other calculogenic material such as porcine submaxillary gland extracts), allowing time for the saliva to partially dry on the surface of the plummet. After a three to five-day dipping period a dental plaque-like deposit is evident, and after about eight or more days of dipping a calculus-like crystalline deposit is found on the surface of the plummet. By treating the plummets daily with the potential anticalculus agents, one can compare the type and extent of deposits appearing on the plummets and deposits appearing on untreated control plummets and in this manner, observations of plaque or calculus formation can be made. The formation of calculus is normally characterized by examining the deposits formed by X-ray crystallography. This examination will show whether the deposits found on the plummet are amorphous or have developed the X-ray pattern characteristic of crystalline hydroxyapatite.

In the screening test using the Leung dipping technique described hereinafter, porcine submaxillary gland extract was employed as a calculogenic agent. Observations of the extent and type of the deposit formation were made after a period of eight days.

(2) The Rat Assay. In the rat assay, rats are fed a calculogenic diet. This diet is generally high in calcium and phosphorus content. The calculus which develops is similar to human calculus in several respects, i.e., molar ratio of calcium to phosphorus, X-ray pattern, infra-red pattern, the nature of noncrystalline impurities, and the degree of mineralization. The agent is evaluated by applying it daily to the molar teeth of the animals over a six-week period (or longer). A control group of animals is treated with an appropriate placebo. At the termination of the experimental period the teeth are scored according to an empirical scale for the extent of calculus accumulation. Activity is expressed in terms of percentage lowering of the test animal score compared to the control score.

(3) The Warburg Test. In the Warburg screen, the percent inhibition of respiration of saliva from a heavy calculus former caused by the addition of the agent is measured. Compounds affecting bacterial growth and metabolism in saliva are detected by this assay.

EXAMPLE 2

Using the foregoing screening techniques, a variety of zinc compounds were tested for anticalculus activity. The following results were obtained:

amount of deposit laid down on the strips during the test period is determined by weighing. During the test, agents were applied as solution or as dentifrices. When agents were tested as mouthwashes, 10 cc were used in each application of 1 minute twice a day under supervision. When tested in toothpaste formulations, 5 cc or 10 cc of a 1:1 water slurry of the dentifrice are used as a mouth rinse twice a day under supervision. Care is observed to insure that the strips are not subjected to the action of a toothbrush since inadvertent brushing could yield spurious results. Controls are established whereby the effects of a placebo can be determined.

TABLE 2

| Compound | Concentration (Aqueous Suspension) | Visual Rating of Deposits (1) | Leung Dipping Test Percent Reduction in Weight of Deposit | X-Ray Analysis (2) | Warburg Test (3) | Rat Assay % Reduction in Calculus |
|---|---|---|---|---|---|---|
| Zinc, n-$C_{14}$-alkyl maleate | 1% | 1 | 16.7% | A | E | 36.3% |
| Zinc tribromo-salicylanilide | 1% | 2 | | A | E | 11.8% |
| | 0.27% | 1.5 | −11.0% | | | 0.25% concentration |
| Zinc 2-hexyl-5-chlorosalicyl-anilide | 1.0% | 3.0 | | No HA | | |
| | 5.0% | 4.5 | 5.8 | No HA | | |
| Zinc stearate | 1.0% | 2.0 | | No HA | | 3.8% |
| | 5.0% | 4.0 | 5.0% | No HA | | 2.0% concentration |
| Zinc carbonate | 1.0% | 3.0 | | No HA | | |
| | 5.0% | 4.0 | | No HA | | |
| Zinc tannate | 1.0% | 4.0 | | A | | |
| | 5.0% | 4.0 | | A | | |
| Zinc caprylate | 0.537% | 3.0 | 14.4 | A | | |
| Zinc octoate | 0.537% | 3.0 | 1.8 | A | | |
| Zinc oleate | 0.961% | 2-½ | 26.1 | A | | |
| Zinc citrate | 0.311% | 2-½ | 28.9 | A | | 42% 5% concentration |
| Zinc laurate | 0.709% | 2-½ | 17.1 | A | | |
| Zinc silicate | 0.159% | | 26.1 | A | | 25.3% 5.0 concentration |

(1) Visual Rating Scale
  Concentration
  1.0 = substantially less than control
  2.0 = moderately less than control
  3.0 = equivalent to control; compound considered active if X-ray shows amorphous
  4.0 = moderately greater than control; compound considered active if X-ray shows amorphous
  5.0 = substantially more than control; compound considered active if X-ray shows amorphous
(2) X-ray Analysis: A = amorphous
  No HA = crystalline material present, but hydroxyapatite absent
  HA = hydroxyapatite detected
(3) S = slightly effective
  E = effective

EXAMPLE 3

Still another screening test which provides useful information is the Mylar strip test. This test is conducted in the following manner:

Contoured, roughened, pre-weighed polyester strips are attached by means of ligatures to the lingual surface of the lower incisor teeth for periods varying from 4 days to 10 days. At the end of the test period the strips are removed and dried for 1 hour at 110° C and the The Mylar strip assay was run in accordance with a crossover design, i.e., half the panel uses the test material first, the remaining using the placebo, and then treatments are reversed for the second half of the test.

A series of tests were conducted using the foregoing procedure. Significant reductions in the formation of deposits were found with the following materials:

TABLE 3

| Active | Vehicle | Control | Mylar Strip Test % Reduction Dry Weight | % Reduction Ash Weight | By No. of Test Days |
|---|---|---|---|---|---|
| Zinc TBS 0.25% | Compatible Toothpaste | Pepsodent Paste | 24.3 (p=<.05) | — | 4 |
| Zinc TBS 0.25% | Mouthwash | Placebo | 33.4 (p=<.01) | — | 10 |
| Zinc citrate 5% | Mouthwash | Placebo | 39.1 (p=<.01) | 47.2 | 10 |
| Zinc TBS 0.25% | (HEC* suspension) | | | | |
| Zinc $C_{12}$-alkyl Benzoyl Acrylate 2%, Zinc TBS 0.25% | Compatible Toothpaste | Placebo Paste | 38.4(p=<.05) | — | 4 |

*HEC = hydroxyethylcellulose

The foregoing invention is further illustrated by the following examples:

EXAMPLE 4

| Ingredients | Weight Percent |
|---|---|
| Abrasive silica (1) | 15.50 |
| Less abrasive silica (2) | 9.00 |
| Zinc 3,4',5-tribromosalicylanilide | 0.25 |
| Refined extract of carrageen | 0.84 |
| Titanium dioxide | 0.5 |
| Saccharin | 0.20 |
| Water | 29.79 |
| Glycerin | 32.00 |
| Polyethylene glycol, m.w. = 400 | 4.00 |
| Sodium hydroxide, 30% solution | 0.10 |
| 21% sodium lauryl sulfate in glycerin | 7.00 |
| Coloring and flavor | 1.32 |

(1) The abrasive silica had an average particle size of 10 microns.
(2) The less abrasive silica had an average particle size of 3 microns.

EXAMPLE 5

| Ingredients | Weight Percent |
|---|---|
| Abrasive silica (1) | 12.00 |
| Less abrasive silica (2) | 6.00 |
| Powdered polyethylene (3) | 5.00 |
| Carboxymethylcellulose | 0.80 |
| Glycerin | 34.37 |
| Saccharin | 0.20 |
| Zinc citrate | 10.00 |
| Zinc tribromosalicylanilide | 0.25 |
| Flavor | 1.30 |
| Coloring | 0.25 |
| Foaming agent | 0.63 |
| Water | 29.20 |

(1) The abrasive silica had an average particle size of 10 microns.
(2) The less abrasive silica had an average particle size of 3 microns.
(3) The polyethylene was a high density polyethylene powder having an average particle size of 8-9 microns.

EXAMPLE 6

| Ingredients | Weight Percent |
|---|---|
| Abrasive silica (1) | 12.00 |
| Less abrasive silica (2) | 5.00 |
| Polyethylene powder (3) | 5.00 |
| Carboxymethylcellulose | 0.80 |
| Zinc 3,4',5-tribromosalicylanilide | 0.25 |
| Zinc citrate | 5.00 |
| Zinc stearate | 5.00 |
| Saccharin | 0.20 |
| Glycerin | 37.03 |
| Flavor | 1.30 |
| Foaming agent | 1.47 |
| Color | 0.25 |
| Water | 26.70 |

(1) The abrasive silica had an average particle size of 10 microns.
(2) The less abrasive silica had an average particle size of 3 microns.
(3) The polyethylene was a high density polyethylene powder having an average particle size of 8-9 microns.

EXAMPLE 7

Dentin Abrasion Test

The test is conducted in the following manner:

(a) Preconditioning to remove surface debris: The radioactive (about one millicurie by exposing the teeth for 2-½ hours to a neutron flux of $5 \times 10^{12}$ neutrons/cm.$^2$, the temperature during irradiation not exceeding 40° C.) specimens of dentin are transferred to the perspex troughs of a standard brushing machine, and their surfaces cleaned of debris, etc. by brushing for 8,000–10,000 double brush strokes in a slurry of calcium pyrophosphate (25 g. solids plus 50 g. of a 1% solution of sodium carboxymethylcellulose containing 10% glycerine).

(b) "Conditioning" the dentin surfaces: Prior to a test run for any particular toothpaste, the specimen surface must be "conditioned" using a slurry of that toothpaste (25 g. paste plus 50 g. of a 1% solution of sodium carboxymethylcellulose-Hercules containing 10% glycerine). The brush has medium nylon bristles, the brush load is 150 g., and the number of double strokes is 1,000. The slurry is poured into a graduated cylinder and the volume of slurry observed.

(c) Test run: After pouring away the "conditioning" slurry as detailed in Section (b) above, the troughs are washed thoroughly in distilled water. A slurry of the same toothpaste is then added to the troughs (same composition as in (b)), and after insuring that the specimen is adequately covered, it is brushed for 1000 strokes.

The active slurry is poured from the trough and any excess foam destroyed. A silicone defoamer is used. After stirring, one 2 ml. sample of the slurry is withdrawn with a pipette, and transferred to aluminum planchets of 1 inch diameter. The slurries are dried ½ hour at 90 ± 5° C.

(d) Order for testing pastes: The order for testing a series of toothpastes is to start and finish with the reference. This insures that the wear rate (with respect to the reference) has not altered from the beginning and end of the whole run. Should there be large differences between the two values for the reference, a reassay is conducted.

(e) Radiotracer counting: The radioactivity of the slurry samples is determined with a Geiger microcounter. To avoid having to make corrections for decay in activity, the counts for all the samples are made within a short period of time. All counts for activity must be corrected for "dead time" and background errors.

(f) Calculation of results: The dentin abrasion value for a particular toothpaste will be the ratio of the corrected counts for that paste to the average count for the reference.

For convenience the reference paste is 25 g. of calcium pyrophosphate paste plus 50 g. of the aqueous gum-glycerine mixture noted above. It is assigned a dentin abrasion value of 475.

The foregoing is a modification of the test given in U.S. Pat. No. 3,538,230 to Lever.

Table 4 illustrates the results of the Dentin Abrasion Test conducted to compare the abrasivity of calcium and magnesium gluconates.

Dentin abrasion values of some commercial dentifrices marketed in 1970, determined by the above method are:

| Toothpaste | Abrasive | Dentin Abrasion Value |
|---|---|---|
| Pepsodent | Dicalcium phosphate dihydrate (40%) plus a precipitated chalk (5%) | 154 |
| Close-Up | Silica xerogel (14%) | 288 |
| A | Calcium pyrophosphate | 264 |
| B | Insoluble sodium metaphosphate | 279 |
| C | Calcium carbonate | 449 |

Samples A, B and C were obtained on the open market.

Table 4

Toothpaste 12803-31A

| Ingredients | Wt. % |
| --- | --- |
| Calcium gluconate | 14.00 |
| Syloid 244* | 7.50 |
| TiO$_2$ | 1.00 |
| Liquid premix** | 68.70 |
| Flavor | 1.80 |
| 21% Sodium dodecylsulfate/79% glycerin | 7.00 |
| | 100.00 |
| Dentin Abrasion Value | 24 |

Toothpaste 12803-31B

| Ingredients | Wt. % |
| --- | --- |
| Magnesium gluconate | 14.00 |
| Syloid 244* | 7.50 |
| TiO$_2$ | 1.00 |
| Liquid premix** | 68.70 |
| Flavor | 1.80 |
| 21% Sodium dodecylsulfate/79% glycerine | 7.00 |
| | 100.00 |
| Dentin Abrasion Value | 24 |

*A silica aerogel having an average particle diameter of about 3 microns.
**Composition of Liquid premix:

| | |
| --- | --- |
| Glycerine | 15.40% |
| Sorbitol (70% sol.) | 47.42% |
| Polyethylene glycol (m.w.1540) | 5.00% |
| Sodium carboxymethylcellulose | 0.30% |
| Saccharin | 0.20% |
| Dye solution (1.2%) | 0.30% |
| Sodium benzoate | 0.08% |

I claim:

1. A method for the control of calculus on tooth surfaces comprising contacting the tooth surfaces at regular intervals with at least one physiologically acceptable zinc compound selected from the group consisting of zinc tribromosalicylanilide, zinc-2-hexyl-5-chlorosalicylanilide, zinc soap of the C$_8$ to C$_{22}$ fatty acids, zinc carbonate, zinc benzoate, zinc dl-lactate trihydrate, zinc citrate, zinc hexafluorosilicate, zinc stannate and zinc silicate, in a physiologically acceptable carrier therefor, said carrier being selected from the group consisting of a mouthwash and a dentifrice composition wherein the abrasives in said dentifrice compositions are substantially free of phosphate and calcium, and wherein said dentifrice has a minimum dentin abrasion value of about 50, the concentration of said zinc compound being effective to reduce the rate of accumulation of calculus, and wherein the maximum concentration of zinc is about 5% by weight of the total composition.

2. A method according to claim 1 wherein said compound is applied at least once daily.

3. A method for the control of calculus on tooth surfaces comprising contacting the tooth surfaces at regular intervals with at least one physiologically acceptable zinc compound selected from the group consisting of zinc tribromosalicylanilide, zinc-2-hexyl-5-chlorosalicylanilide, zinc soap of the C$_8$ to C$_{22}$ fatty acids, zinc carbonate, zinc benzoate, zinc dl-lactate trihydrate, zinc citrate, zinc oxide, zinc hexafluorosilicate, zinc stannate and zinc silicate, in a physiologically acceptable mouthwash, the concentration of such zinc compound in said mouthwash being effective to reduce the rate of accumulation of calculus, and wherein the maximum concentration of zinc is about 5% by weight of the total composition.

4. A method according to claim 1 wherein said carrier is a dentifrice composition.

5. A dental composition for controlling the accumulation of calculus on tooth surfaces comprising at least one physiologically acceptable zinc compound selected from the group consisting of zinc tribromosalicylanilide, zinc-2-hexyl-5-chlorosalicylanilide, zinc soap of the C$_8$ to C$_{22}$ fatty acids, zinc carbonate, zinc benzoate, zinc dl-lactate trihydrate, zinc citrate, zinc hexafluorosilicate, zinc stannate and zinc silicate, in a physiologically acceptable carrier therefor, said carrier being selected from the group consisting of a mouthwash and a dentifrice composition, wherein the abrasives in said dentifrice composition are substantially free of phosphate and calcium, and wherein said dentifrice has a minimum dentin abrasion value of about 50, the concentration of said zinc compound being effective to reduce the rate of accumulation of calculus, and wherein the maximum concentration of zinc is about 5% by weight of the dental composition.

6. A dental composition for controlling the accumulation of calculus on tooth surfaces comprising at least one physiologically acceptable zinc compound selected from the group consisting of zinc tribromosalicylanilide, zinc-2-hexyl-5-chlorosalicylanilide, zinc soap of the C$_8$ to C$_{22}$ fatty acids, zinc carbonate, zinc benzoate, zinc dl-lactate trihydrate, zinc citrate, zinc oxide, zinc hexafluorosilicate, zinc stannate and zinc silicate, in a physiologically acceptable mouthwash, the concentration of said zinc compound being effective to reduce the rate of accumulation of calculus, the maximum concentration of zinc being about 5% by weight of said mouthwash composition.

7. A dental composition according to claim 5 wherein said carrier is a dentifrice composition.

8. A composition according to claim 6 wherein said mouthwash comprises water and a minor amount of the physiologically acceptable suspending agent for said zinc compound, the concentration of said zinc compound being from about 1/10% to about 25% by weight.

9. A composition according to claim 5 wherein said carrier is a dentifrice comprising a dental abrasive and the concentration of said zinc compound is from about 1/4% to about 25% by weight.

10. A composition according to claim 8 wherein the amount of said zinc compound is between about 1/10% and about 5% by weight of said composition.

11. A composition according to claim 9 wherein said zinc compound is between about 1/4% and about 10% by weight of said composition.

12. A method according to claim 1 wherein said zinc compound is zinc tribromosalicylanilide.

13. A method according to claim 1 wherein said zinc compound is zinc-2-hexyl-5-chlorosalicylanilide.

14. A method according to claim 1 wherein said zinc compound is zinc soap of the C$_8$ to C$_{22}$ fatty acids.

15. A method according to claim 1 wherein said zinc compound is zinc carbonate.

16. A method according to claim 1 wherein said zinc compound is zinc benzoate.

17. A method according to claim 1 wherein said zinc compound is zinc dl-lactate trihydrate.

18. A method according to claim 1 wherein said zinc compound is zinc citrate.

19. A method according to claim 1 wherein said zinc compound is zinc hexafluorosilicate.

20. A method according to claim 1 wherein said zinc compound is zinc stannate.

21. A method according to claim 1 wherein said zinc compound is zinc silicate.

22. A dental composition according to claim 5 wherein said zinc compound is zinc tribromosalicylanilide.

23. A dental composition according to claim 5 wherein said zinc compound is zinc-2-hexyl-5-chlorosalicylanilide.

24. A dental composition according to claim 5 wherein said zinc compound is zinc soap of the $C_8$ to $C_{22}$ fatty acids.

25. A dental composition according to claim 5 wherein said zinc compound is zinc carbonate.

26. A dental composition according to claim 5 wherein said zinc compound is zinc benzoate.

27. A dental composition according to claim 5 wherein said zinc compound is zinc dl-lactate trihydrate.

28. A dental composition according to claim 5 wherein said zinc compound is zinc citrate.

29. A dental composition according to claim 5 wherein said zinc compound is zinc hexafluorosilicate.

30. A dental composition according to claim 5 wherein said zinc compound is zinc stannate.

31. A dental composition according to claim 5 wherein said zinc compound is zinc silicate.

* * * * *

UNITED STATES PATENT OFFICE
CERTIFICATE OF CORRECTION

Patent No. 4,100,269      Dated July 11, 1978

Inventor(s) Morton Pader

It is certified that error appears in the above-identified patent and that said Letters Patent are hereby corrected as shown below:

First page, line 4 of Item 63, "800,008" should read -- 808,008 --;
Column 1, line 7, "800,008" should read -- 808,008 --;
Column 3, line 3, "water," should read -- water. --;
Column 4, line 58, "substantable" should read -- substantive --;
Column 6, line 23, "this purposes" should read -- these purposes --.

Signed and Sealed this

Twentieth Day of March 1979

[SEAL]

Attest:

RUTH C. MASON
Attesting Officer

DONALD W. BANNER
Commissioner of Patents and Trademarks